(12) United States Patent
Boettner et al.

(10) Patent No.: US 10,238,454 B2
(45) Date of Patent: Mar. 26, 2019

(54) FLUOROSCOPY-BASED TECHNIQUE TO MEASURE INTRAOPERATIVE CUP ANTEVERSION

(71) Applicant: Friedrich Boettner, Larchmont, NY (US)

(72) Inventors: Friedrich Boettner, Larchmont, NY (US); Matthieu Zingg, Geneva (CH)

(73) Assignee: Friedrich Boettner, Larchmont, NY (US)

( * ) Notice: Subject to any disclaimer, the term of this patent is extended or adjusted under 35 U.S.C. 154(b) by 0 days.

(21) Appl. No.: 15/501,671

(22) PCT Filed: Aug. 5, 2016

(86) PCT No.: PCT/US2016/045710
§ 371 (c)(1),
(2) Date: Feb. 3, 2017

(87) PCT Pub. No.: WO2017/024202
PCT Pub. Date: Feb. 9, 2017

(65) Prior Publication Data
US 2017/0224418 A1 Aug. 10, 2017

Related U.S. Application Data

(60) Provisional application No. 62/201,417, filed on Aug. 5, 2015.

(51) Int. Cl.
| | | |
|---|---|---|
| A61B 34/10 | (2016.01) | |
| A61B 6/12 | (2006.01) | |
| A61F 2/34 | (2006.01) | |
| A61B 5/107 | (2006.01) | |
| A61B 6/00 | (2006.01) | |
| A61B 5/00 | (2006.01) | |
| A61F 2/46 | (2006.01) | |

(Continued)

(52) U.S. Cl.
CPC .............. *A61B 34/10* (2016.02); *A61B 5/107* (2013.01); *A61B 5/1077* (2013.01); *A61B 5/4528* (2013.01); *A61B 6/12* (2013.01); *A61B 6/4441* (2013.01); *A61B 6/4482* (2013.01); *A61B 6/505* (2013.01); *A61B 6/5217* (2013.01); *A61F 2/34* (2013.01); *A61F 2/4657* (2013.01); *A61B 34/20* (2016.02); *A61B 34/32* (2016.02); *A61B 2034/2065* (2016.02); *A61B 2090/376* (2016.02); *A61F 2002/4658* (2013.01); *A61F 2002/4668* (2013.01)

(58) Field of Classification Search
CPC .............................. A61B 6/4441; A61B 34/10
See application file for complete search history.

(56) References Cited

U.S. PATENT DOCUMENTS

| | | |
|---|---|---|
| 9,056,020 B1 | 6/2015 | Termanini |
| 2004/0087852 A1 | 5/2004 | Chen et al. |

(Continued)

*Primary Examiner* — Olivia C Chang
(74) *Attorney, Agent, or Firm* — Leason Ellis LLP

(57) ABSTRACT

Direct anterior approach (DAA) with the patient lying supine has facilitated the use of intraoperative fluoroscopy and allows for standardized positioning of the patient. The method disclosed herein uses intraoperative fluoroscopy to measure acetabular component anteversion and more particularly, a method for measuring/calculating intraoperative cup (acetabular component) anteversion is provided based on the measured acetabular component abduction angle and a c-arm tilt angle (CaT).

20 Claims, 10 Drawing Sheets

(51) Int. Cl.
 *A61B 34/20* (2016.01)
 *A61B 90/00* (2016.01)
 *A61B 34/32* (2016.01)

(56) References Cited

U.S. PATENT DOCUMENTS

2011/0144704 A1 6/2011 Switzer
2015/0088146 A1 3/2015 McCarthy
2015/0238271 A1 8/2015 Wollowick et al.

FLUOROSCOPY-BASED TECHNIQUE TO MEASURE INTRAOPERATIVE CUP ANTEVERSION

CROSS-REFERENCE TO RELATED APPLICATION

The present application is a U.S. National Phase Application under 35 U.S.C. § 371 of International Patent Application No. PCT/US16/45710, filed Aug. 5, 2016, which claims priority to U.S. patent application Ser. No. 62/201,417, filed Aug. 5, 2015, each of which is hereby incorporated as if expressly set forth in their respective entirety herein.

TECHNICAL FIELD

The present invention relates to total hip arthroplasty (THA) and more specifically, relates to a direct anterior approach (DAA) in which the patient lies in a supine position and a method for measuring/calculating intraoperative cup (acetabular component) anteversion based on the measured acetabular component abduction angle and a C-arm tilt angle (CaT).

BACKGROUND

Total hip arthroplasty (THA) (also called surgical replacement of the hip joint with an artificial prosthesis (total hip replacement)) is a reconstructive procedure in which the damaged bone and cartilage are removed and replaced with prosthetic components. Total hip arthroplasty is an often chosen treatment option for people with late-stage degenerative hip disease; however, chronic pain and impairment of daily function of patients with severe hip arthritis are also reasons for considering treatment with total hip replacement.

In THA, one of the components that is needed to reconstruct the hip is an acetabular cup which is used to replace the natural socket of the patient which is called the acetabulum. The acetabular cup is the part of the hip implant that forms the socket in the ball-and-socket structure of the hip joint. The femoral head at the top of the femur rotates within the curved surface of the acetabulum. Accordingly, the THA procedure involves replacing the acetabulum (socket) with the acetabular cup and a femoral implant that includes a femoral head (ball) and a stem that attaches to the femur bone.

Implant positioning is of critical importance in primary total hip arthroplasty. Acetabular cup position is traditionally described by its centre of rotation (acetabular component offset), its anteversion (CV), and its inclination (CI, also termed abduction). Incorrect acetabular cup placement is associated with higher dislocation rates, range of motion limitations due to impingement, eccentric polyethylene wear, and ultimately, higher rates of revision.

Conventional techniques used to determine acetabular cup position include external alignment guides, free-hand positioning and the use of anatomic landmarks. Previous studies demonstrated that these techniques allow for correct positioning of the acetabular component in the target zone in only 50-86% of the cases. In order to avoid implant malposition, a variety of imageless and image-based navigation techniques have been developed.

More specifically, perioperative imageless techniques are primarily based on infrared optical stereoscopy and involve an optical localizer capturing the position of an optical tracker, which is fixed to the patient thus allowing for the three-dimensional tracking of tools and prosthetic components. These methods do not expose the patient to radiation nor do they require a specific patient position, but they necessitate costly dedicated hardware and perioperative registration and calibration procedures that are time consuming. In combination with surface mapping based on Computer Tomography (CT) images this technology is also used in robotic assisted surgery.

As mentioned herein, one surgical technique for THA is referred to as the direct anterior approach (DAA). In general, direct anterior hip replacement is a minimally invasive surgical technique which involves a 3 to 4 inch incision on the front of the hip that allows the joint to be replaced by moving muscles aside along their natural tissue planes, without detaching any tendons. The introduction of the direct anterior approach (DAA) with the patient lying in a supine position has greatly facilitated the use of intraoperative fluoroscopy. As is known, fluoroscopy is a type of medical imaging that shows a continuous X-ray image on a display (monitor), much like an X-ray movie. During a fluoroscopy procedure, an X-ray beam is passed through the body.

Fluoroscopic control during THA provides standardized anterior posterior (AP) images of the hip, which can improve acetabular cup placement. However, the assessment of the CV (anteversion) angle has proven to be more complicated. Image-based techniques relying on standardized AP pelvic films such as those introduced by Lewinnek and Liaw have been validated but are not easily available intraoperatively.

There is therefore a need for an improved method for determining acetabular anteversion using intraoperative fluoroscopy for patients undergoing anterior or anterolateral total hip replacement in a supine position.

SUMMARY

A fluoroscopy-based method for measuring intraoperative acetabular cup anteversion during total hip arthroplasty utilizing a direct anterior approach (DAA) comprising the steps of:

(a) positioning a patient in a supine position on a support surface and positioning the acetabular cup in an initial implant position within the patient;

(b) positioning a C-arm fluoroscopic system in an initial position perpendicular to a longitudinal axis of the support surface;

(c) generating an anterior posterior (AP) image of a pelvis of the patient;

(d) measuring an abduction angle of the acetabular cup using the anterior posterior (AP) image of the pelvis;

(e) moving the C-arm of the fluoroscopic system out of the initial position an in a directed away from a hip of the patient that is being replaced with an implant until the C-arm reaches a target position in which an equatorial plane of the acetabular cup is perpendicular to a plane of the image amplifier (fluoroscopy receptor of the C-arm) in an external pelvic oblique radiographic image;

(f) recording a C-arm tilt angle when the C-arm is in the target position;

(g) calculating an anteversion angle based on the measured abduction angle and the recorded C-arm tilt angle; and (h) determining if the calculated anteversion angle is within a predetermined acceptable range and if the calculated anteversion angle is outside of the predetermined acceptable angle, then steps (a)-(h) are repeated until the calculated anteversion angle is within the predetermined acceptable range.

BRIEF DESCRIPTION OF DRAWING FIGURES

FIG. 1 is a perspective view of a hip area of a patient in which $\vec{n}_{rim}$ is the vector normal to the equatorial plane of the cup and is defined by the inclination angle CI and the anteversion angle CV; aCV is the angle between the projection of $\vec{n}_{rim}$ on the transverse plane and the coronal plane; $\vec{n}_{ia}$ is the vector normal to the plane of the image amplifier; and CaT is the tilt angle that needs to be applied to the c-arm to make the plane of the image amplifier perpendicular to the cup equatorial plane (it corresponds to the angle between $\vec{n}_{ia}$ and the z-axis);

FIG. 2 illustrates two equivalent aCV measuring techniques on CT-scan images in which the reference line of the coronal plane passes through the ischial spines; aCV is the angle between the coronal plane and the line perpendicular to the equatorial plane of the cup (green); and aCV is the angle between a line parallel to the sagittal plane and a line parallel to the equatorial plane of the cup (red);

DETAILED DESCRIPTION OF CERTAIN EMBODIMENTS

Figure 1:
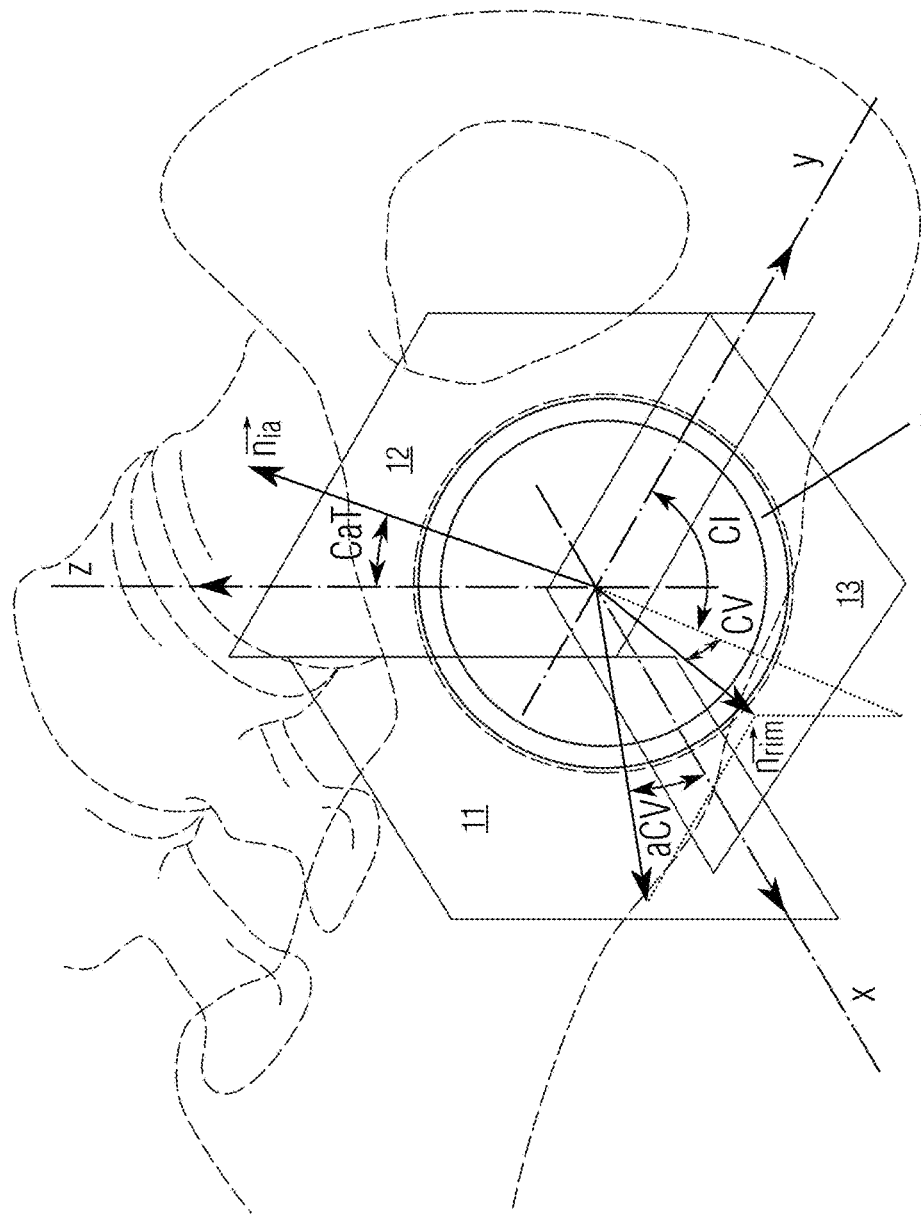

When describing the position (orientation) of the acetabular cup, CV and CI refer to Murray's radiographic definition of anteversion and inclination, respectively, as shown in FIG. 1. In FIG. 1, $\vec{n}_{rim}$ is the vector normal to the equatorial plane of an acetabular cup 10 and is defined by the inclination angle CI and the anteversion angle CV. aCV is the angle between the projection of $\vec{n}_{rim}$ on a transverse plane 11 and a coronal plane 13. $\vec{n}_{ia}$ is the vector normal to the plane of the image amplifier of the C-arm. CaT is the tilt angle that needs to be applied to the C-arm to make the plane of the image amplifier perpendicular to the cup equatorial plane. It corresponds to the angle between $\vec{n}_{ia}$ and the z-axis. The sagittal plane is shown at 12.

CV is thus defined as the angle between the vector perpendicular to the equatorial plane of the cup and the coronal plane 13. CI is thus defined as the angle between the sagittal plane 12 and the projection of the vector perpendicular to the equatorial plane of the cup on the coronal plane 13. Murray's definition of the anatomic anteversion angle (aCV) corresponds to the angle between the coronal plane 13 and the projection of the vector perpendicular to the equatorial plane of the cup 10 on the transverse plane 11. As CV and aCV are different projections of the same vector, they are dependent and bound by the relation:

$$CV=\tan^{-1}[\tan(aCV)\sin(CI)]$$

Figure 2:
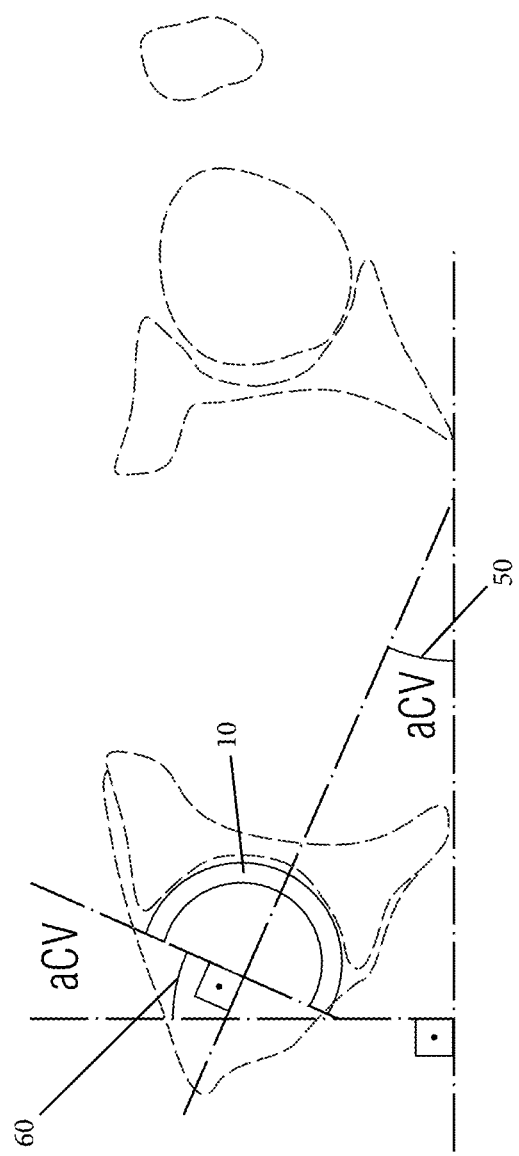

This relation proves useful to compare experimental and control (CT-scan) cup anteversion assessment methods because the evaluation of CV on CT-scan images is challenging whereas the measurement aCV is straightforward as depicted in FIG. 2. FIG. 2 presents two equivalent aCV measuring techniques on CT-scan images. The reference line of the coronal plane passes through the ischial spines. aCV is the angle between the coronal plane and the line perpendicular to the equatorial plane of the cup (as depicted at 50). aCV is the angle between a line parallel to the sagittal plane and a line parallel to the equatorial plane of the cup (as depicted at 60).

Intraoperative Technique According to Present Invention

As mentioned herein, the present invention is directed to an improved system and method for determining acetabular anteversion using intraoperative fluoroscopy for patients undergoing anterior or anterolateral total hip replacement in a supine position. This method consists of a number of steps that are each described in detail herein and in which the patient is in a supine position.

Figure 3B:
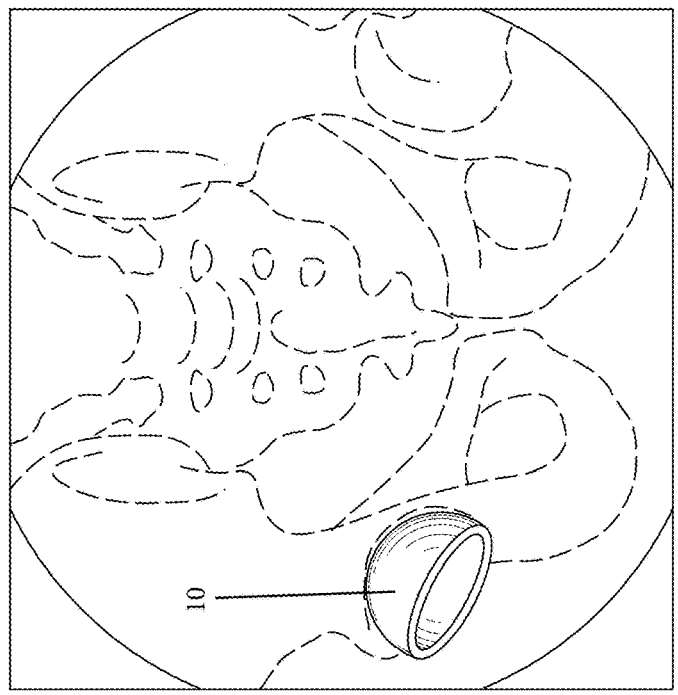
FIG. 3B is an anteroposterior (AP) image (radiograph) of the pelvis showing that in this view, the acetabular cup rim appears elliptical.
Figure 3A:
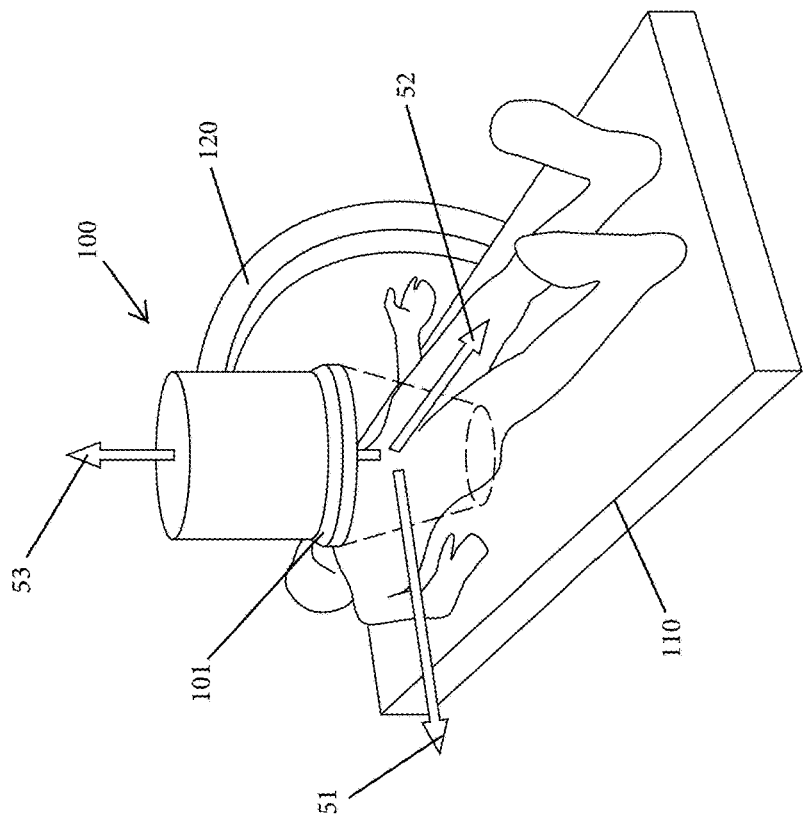
FIG. 3A is a perspective view of a fluoroscopic system positioned perpendicular to a longitudinal axis of the operating table.

FIG. 3A illustrates an exemplary imaging system (or "fluoroscopy system") 100 that comprises an x-ray imaging system in the form of a fluoroscope. The fluoroscopy system 100 includes an x-ray image intensifier (image amplifier) 101 that is configured to convert x-rays into visible light at higher intensity than mere fluorescent screens do. The image intensifier 101 allows low-intensity x-rays to be converted to a conveniently bright visible light output. The fluoroscopy system 100 traditionally contains a low absorbency/scatter input window, typically aluminum, input fluorescent screen, photocathode, electron optics, output fluorescent screen and output window. These parts are all typically mounted in a high vacuum environment within glass or more recently, within metal/ceramic. By its intensifying effect, the fluoroscopy system 100 allows the viewer to more easily see the structure of the object being imaged than fluorescent screens alone, whose images are dim.

The exemplary imaging system 100 shown in FIG. 3A is configured as a C-arm based system, which is commonly used for studies requiring the maximum positional flexibility. The fluoroscopy system 100 has a patient support (e.g., a table) 110 which allows the patient to lie in a supine position. The fluoroscopy system 100 also includes a C-arm unit 120 (which has a "C" shape) that is positioned relative to and is movable relative to the table 110. The fluoroscopy system 100 also includes other devices and more particularly, an imaging device/control console 130 (FIG. 3C), one or more display monitors 190 and image processing and recording devices, and a workstation 195 which can be detached and remote from the C-arm 120.

Imaging device/control console 130 can perform many different movements of the C-arm 120. For example, the C-arm 120 has the following range of movements: raise, lower, extend, rotate and tilt.

The workstation 195 can be configured as a standalone unit or an integrated component within the fluoroscopy system 100. In one or more embodiments, operation of the C-arm 120 is navigated at the workstation 195 and can include the following: power switch, exposure switch, brake pedal, controls radiographic settings, fluoroscopic settings, hard disk, optical disk, writer/rewriter, DVD-R/RW-PACS, advanced image quality enhancement software, noise reduction, zoom control, save and swap images, and single or dual monitors.

The C-arm 120 is defined by a curved arm with an x-ray tube (x-ray source) mounted on one end of the arm and the image intensifier 101 (image amplifier) or flat-panel digital detector on the other end of the arm. The image amplifier 101 is defined by a plane that passes therethrough as discussed herein. As mentioned herein, the C-arm 120 is constructed so that it is movable in a controlled manner relative to the support table 110 and thus relative to the patient. In some embodiments, the C-arm 120 can perform both linear and rotating motions for optimum positioning with respect to the patient. In one or more embodiments, the fluoroscopy system 100 uses a camera (e.g., I/O device 170) to scan and transmit the radiographic image to a remote display monitor (e.g., processor 150 instructs display controller 180 to display the image on display monitor 190). Flat-panel detectors use a scintillator material to convert x-rays to visible light, which is translated into a signal suitable for digital display. It will be appreciated that the foregoing is only a description of one exemplary system 100.

The C-arm 120 works in conjunction with patient table 110 that is specifically designed for X-ray imaging. The table 110 allows for free positioning of the C-arm 120 around the patient. The table 110 is also X-ray translucent so as to not interfere with imaging.

In FIG. 3A, the fluoroscopy system (C-arm 120) is positioned perpendicular to the longitudinal axis of the operating table 110. In FIG. 3B, an anteroposterior view of the pelvis is shown and it will be appreciated that the acetabular cup rim appears elliptical in such view with the patient lying in the supine position on table 110.

In one or more embodiments, the fluoroscopy system 100 employs hardware and software that provide functionality to measure intraoperative acetabular cup anteversion during total hip arthroplasty. Computer programs (and other executable instructions) and data can be stored on a machine-readable medium that is accessible by one or more processors 150 for providing functionality shown and described herein. Various forms of computing devices are accessible to the network 107 and can communicate over the network to the various machines that are configured to send and receive content, data, as well as instructions that, when executed, enable operation of C-arm unit 120. The content and data can include information in a variety of forms, including, as non-limiting examples, text, audio, images, and video, and can include embedded information such as links to other resources on the network, metadata, and/or machine executable instructions. Each computing device can be of conventional construction, and while discussion is made in regard to servers that provide different content and services to other devices, such as mobile computing devices 105, one or more of the server computing devices 109 can comprise the same machine or can be spread across several machines in large scale implementations, as understood by persons having ordinary skill in the art. In relevant part, each computer server has one or more processors, a computer-readable memory that stores code that configures the processor to perform at least one function, and a communication port for connecting to the network 107. The code can comprise one or more programs, libraries, functions or routines which, for purposes of this specification, can be described in terms of a plurality of modules, residing in a representative code/instructions storage, that implement different parts of the process described herein.

Further, computer programs (also referred to herein, generally, as computer control logic or computer readable program code) can be stored in a main and/or secondary memory and implemented by one or more processors (controllers, or the like) to cause the one or more processors to perform the functions of the invention as described herein. In this document, the terms "memory," "machine readable medium," "computer program medium" and "computer usable medium" are used to generally refer to media such as a random access memory (RAM); a read only memory (ROM); a removable storage unit (e.g., a magnetic or optical disc, flash memory device, or the like); a hard disk; or the like.

Figure 3C:
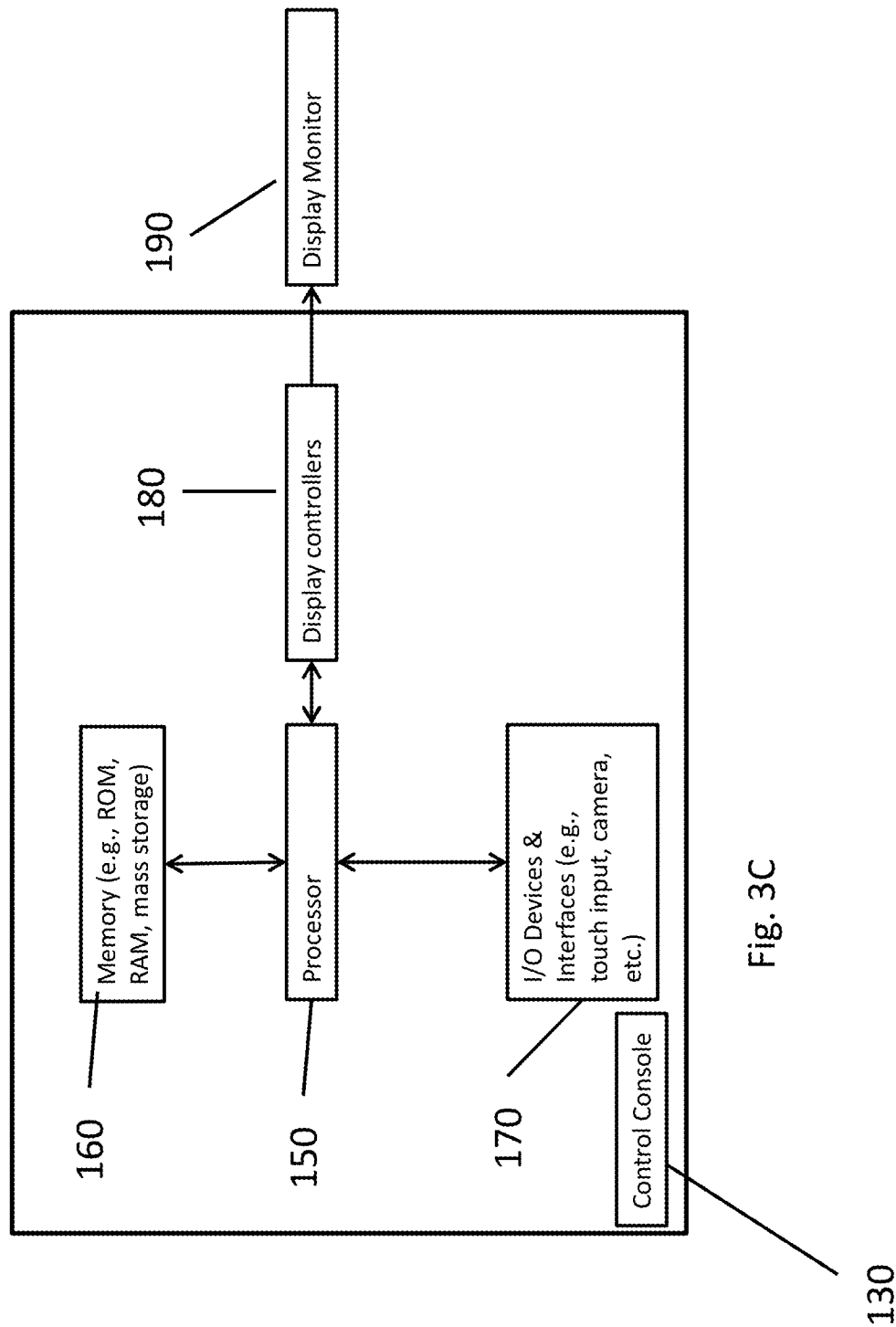
FIG. 3C is a block diagram illustrating an exemplary hardware arrangement included with the fluoroscopic system of FIG. 3A.

With reference now to FIG. 3C, a block diagram is provided of an example hardware arrangement that operates as the control console 130 for fluoroscope 100. In one or more embodiments, the control console 130 is physically integrated with C-arm 120, resides in a structure entirely separate from the C-arm, or is partially integrated with the C-arm and partially separate. The control console 130 (occasionally collectively or individually referred to herein as "processor") can include one or more data processing apparatuses that can include, for example, mobile computing devices 105 such as tablet computing devices, smartphones, personal digital assistants or the like, as well as laptop computers and/or desktop computers. In other embodiments, the control console 130 may be a network computer 109, 195 or an embedded processing apparatus within another device or consumer electronic product. As noted herein, the control console 130 can be configured to access one or more databases such as provided in memory 160, and usable the present application. Such databases can include, for example, image files, video content, documents, audio/video recordings, metadata and other information. For example, the control console 130 can store radiographs or anteversion measurements made by the fluoroscopy system 100. Control console 130 can also communicate with devices comprising databases using any known communication method, including a direct serial, parallel, universal serial bus ("USB") interface, or via a local or wide area network.

Figure 3D:
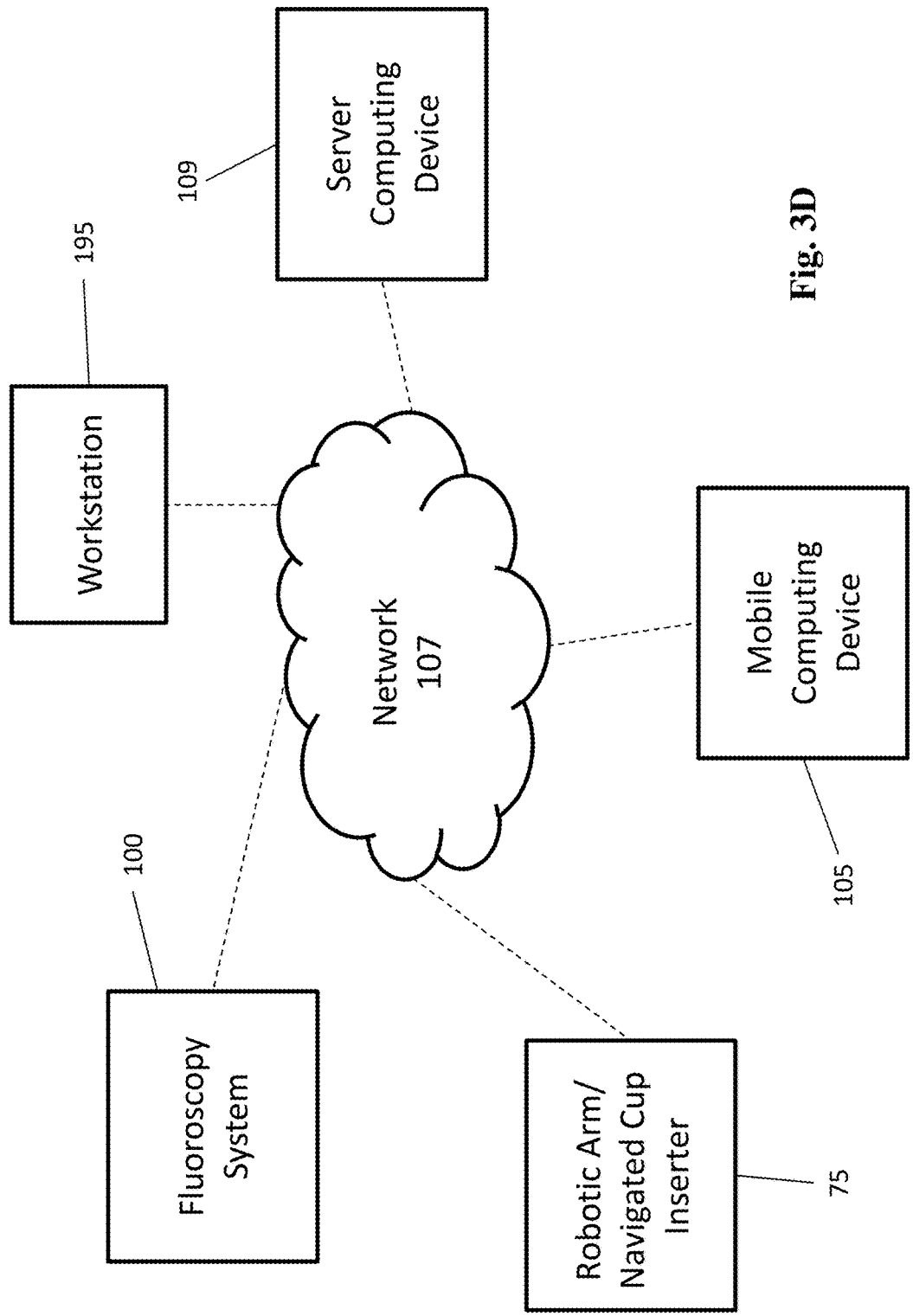
FIG. 3D is a block diagram illustrating an exemplary network configuration in connection with an example embodiment of the present application.

In one embodiment disclosed herein as shown in FIG. 3D, the fluoroscopy system 100 communicates with a main or server computing device 109 and/or a mobile computing device 105 (e.g., a tablet) over a communications network 107 to allow the surgeon (or other user) to view the images (radiographic images) generated by the fluoroscope and also permit, via a user interface, the user to provide input that is used to calculate certain angles (inputs) that are used to calculate the anteversion angle of the cup 10. These details are described in more detail herein. This arrangement allows for the surgeon to view substantially in real-time radiographic images of the surgical site including the acetabular cup position and also allows the surgeon to control certain movements of the surgical equipment. In other arrangements, the actual subsequent cup positioning step(s) can be performed by a user controlled robotic arm or navigated insertion tool (navigated cup inserter) that communicates with and receives control signals from a processor 150 (e.g., associated with a server computing device).

In one or more embodiments, the control console 130 can provide at least some of the functionality in accordance with the teachings herein. Control console 130, server computing device 109 and/or mobile computing device 105 can be configured to include one or more microprocessors 150 and/or other connected system components (e.g., multiple connected chips) or the control console 130 may be configured with system-level on a chip.

As noted herein, the control console 130, server computing device 109 and/or mobile computing device 105 includes memory 160 (e.g., non-transitory processor readable media) which is accessible and/or coupled to the processor(s) 150. The memory 160 may be used for storing data, metadata, and programs for execution by the microprocessor(s) 150. The memory 160 may include one or more of volatile and non-volatile memories, such as Random Access Memory ("RAM"), Read Only Memory ("ROM"), Flash, Phase Change Memory ("PCM"), or other type.

The control console 130 can also be configured to include one or more input or output ("I/O") devices and interfaces 170, which are provided to allow a user to provide input to, receive output from, and otherwise transfer data to and from the system. These I/O devices may include a mouse, keypad or a keyboard, a touch panel or a multi-touch input panel, camera, network interface, modem, other known I/O devices or a combination of such I/O devices. The touch input panel may be a single touch input panel which is activated with a stylus or a finger or a multi-touch input panel which is activated by one finger or a stylus or multiple fingers, and the panel is capable of distinguishing between one or two or three or more touches and is capable of providing inputs derived from those touches to the control console 130. The I/O devices and interfaces 170 may include a connector for a dock or a connector for a USB interface, FireWire, etc. to connect the system 100 with another device, external component, or a network.

Moreover, a display controller 180 and display device 190 can provide a visual user interface for the user; this user interface may include a graphical user interface which, for example, is similar to that shown on a desktop, laptop, tablet or mobile device when running Mac OS, Windows OS, Android, Linux, or other common operating system software. Further, one or more buses can be included that interconnect various modules, such as illustrated in the block diagram shown in FIG. 3C.

It will be appreciated that additional components, not shown, may also be part of or otherwise accessible to the control console 130, and, in certain embodiments, fewer components than that shown in FIG. 3C may also be used in control console 130. The computer-implemented methods may be carried out in a computer system or other data processing system in response to its processor or processing system executing sequences of instructions contained in a memory, such as memory 160 or other machine-readable storage medium. In various embodiments, hardwired circuitry may be used in combination with the software instructions to implement the present embodiments. Thus, the techniques are not limited to any specific combination of hardware circuitry and software, or to any particular source for the instructions executed by the control console 130.

As mentioned herein, in one or more embodiments, a robotic implementation of the present invention is provided such that the acetabular cup 10 can be grasped by a controllable robotic arm 75 (FIG. 3D). The controllable robotic arm 75 can include or otherwise be accessible by processors and communication modules that are in communication over network 107 with one or more of the fluoroscopy system 100, the main computing device 109, and the mobile computing device 105. The robotic arm 75 can be configured with one or more robotic grippers that are each configured to grasp a handle (post) that is coupled to the acetabular cup 10 to allow for repositioning of the acetabular cup 10 relative to the patient's body. The robotic arm 75 can thus either control: cup position, or direct the C-arm 120. Alternatively, a navigated instrument can be directed to help adjust the cup position until the cup is in line (in registration) with the data (e.g., visual radiographic image guidance, an output indicating target cup position achieved, etc.) provided by the control panel. In other words, the navigated instrument is in communication with the hardware described herein and can be configured to adjust the position of the acetabular cup 10. Since the navigated instrument includes navigational markers, the location of the navigated instrument can be calculated and since the navigated instrument is coupled to the cup, the cup's movements can be detected and measured. The control console or other hardware described herein can thus provide instructions (which can be displayed on the display) to the user directing how the acetabular cup should be positioned and/or repositioned with the patient.

The robotic arm 75 can further include navigational markers (e.g., tracking elements) and navigation software can be executed via one or more processors to control the movement of the robotic arm 75. In addition, one or more tracking elements can be associated with the patient (i.e., can be coupled to a bone (e.g., pelvis bone) of the patient) to allow for measurement and tracking of not only the location of the robotic arm and thus, the acetabular cup 10 but also the location and position of the patient (e.g., pelvic bone). In this manner, the robotic arm 75 can be controlled and moved relative to the surrounding anatomical landscape to allow for positioning and/or repositioning of the acetabular cup 10.

In accordance with the present invention, an exemplary anteversion measurement technique (measurement method) requires the patients to be positioned in a supine position and involves the following steps. It will be appreciated that the order of the steps can be altered and therefore, the order of the steps disclosed herein is only exemplary in nature and is not limiting of the scope of the claimed invention. In one exemplary embodiment, as set forth below, the method for determining intraoperative cup anteversion includes three distinct steps each of which is described below.

Determination of the Abduction Angle

To begin (in an exemplary operation), the fluoroscopy system 100 (i.e., the C-arm 120 thereof) is positioned perpendicular to the longitudinal axis of the patient and the operating room table 110 as shown in FIG. 3A. The patient is thus in the supine position. Next, an anteroposterior (AP) pelvic view is taken using the fluoroscopy system 100. FIG. 3B shows an exemplary AP pelvic view.

As discussed herein, the abduction angle can be defined as the angle between the sagittal plane and the projection of the vector perpendicular to the equatorial plane of the cup on the coronal plane (see, FIG. 1).

In accordance with the present invention, the abduction angle is measured using a suitable technique, such as by using a protractor, or the angle can be visually evaluated on display 190. For example, the abduction angle can be measured using an ordinary protractor on an anteroposterior (AP) radiographic image. It will be understood that as used herein, a radiographic image includes but is not limited to a radiographic image of the surgical site of interest that is displayed on screen and can be stored in memory and also to a physical printout/physical manifestation (e.g., radiographic film) of the radiographic image.

In one or more embodiments, the abduction angle is measured by a computer system (e.g., a mobile computing device 105 or control console 130 or server computing device 109) that is configured with image-analysis software. For example, the anteroposterior (AP) radiographic image is displayed on a display 190 of a mobile computing device 105 (e.g., a tablet) or on the display 190 of a control console 130 via an interactive user interface. One or more modules configure the device 105/130 to determine the abduction angle and presents information representing the abduction angle to the user (e.g., surgeon). For example, the user interface provided via one or more modules executing on device 105/130/109 can superimpose a sagittal plane and a coronal plane on the radiographic image (AP pelvic view) manually by receiving inputs from the user or substantially automatically by executing one or more modules. In addition, the equatorial plane of the acetabular cup on the coronal plane can be superimposed on the radiographic image and a projection of the vector perpendicular to the equatorial plane of the cup on the coronal plane can be established. These superimposed planes and the vector projection can be identified with appropriate indicia/markings (e.g., different coloured translucent planes that are individually identified by indicia) on the radiographic image. These reference planes and markings can be manipulated by the user, such as by hand movements along a touch screen of the mobile computing device, adjustments using a joystick, mouse, trackball or other pointing/selection/input device, in order to adjust the locations or otherwise alter the appearance thereof.

Once the reference planes and reference markings are superimposed over the radiographic image, angle measurement tools executing by processor calculates the inclination angle (CI). For example, the user can use a virtual ("digital") protractor tool to calculate the inclination angle (CI) between selected reference planes/reference markings displayed in the radiographic image. It will be appreciated that other tools can be used to calculate such angle, and the angle can be provided without a graphical representation.

In addition, the mobile computing device 105 can be configured by executing one or more software modules to instruct the user to highlight certain reference points, such as the reference planes discussed above, and these highlighted points are usable as data inputs that are then used to calculate the inclination angle. For example, once prompted, the user can identify one reference point, such as the reference plane, and once a sufficient number of reference points have been identified by the user, the program is able to calculate the angle between the identified reference points (i.e., between the sagittal plane and the projection of the vector perpendicular to the equatorial plane of the cup on the coronal plane).

Once calculated, the inclination angle (CI) can be displayed to the user via the user interface and/or stored in memory for later processing to calculate the anteversion angle using the method disclosed herein.

Determination of the C-Arm Tilt Angle (CaT)

Figure 4B:
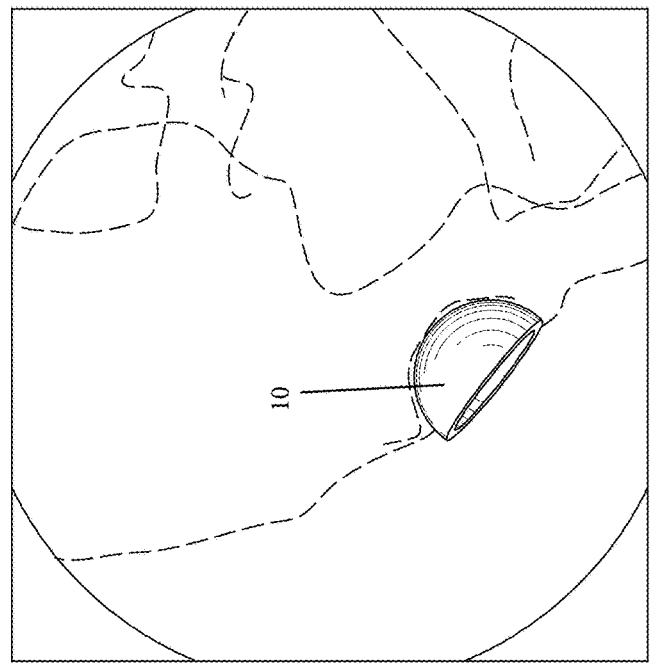
FIG. 4B illustrates that in the position of FIG. 4A, the acetabular rim looks linear and no longer elliptical.
Figure 4A:
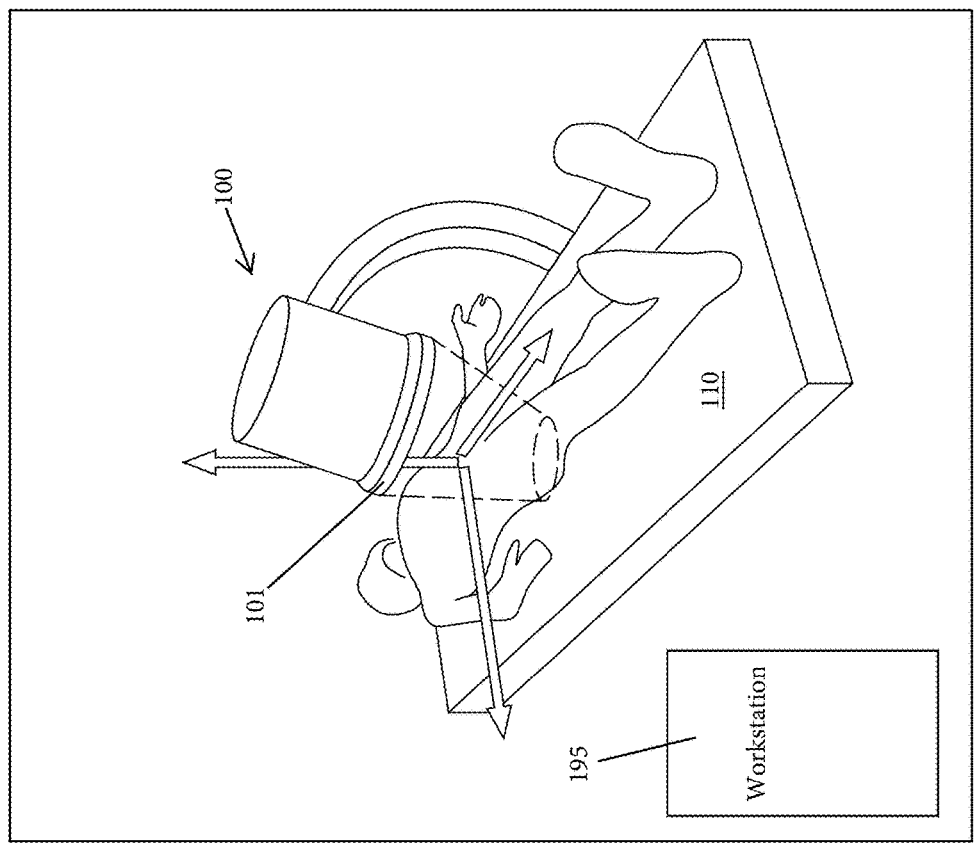
FIG. 4A shows the C-arm of the fluoroscopic system tilted around the cranio-caudal axis such that the plane of the acetabular cup rim is perpendicular to the plane of the image amplifier.

As part of a process to determine the C-arm tilt angle, the C-arm 120 is moved over the hip of the patient and gradually tilted away from the operated side in the same way one would do to obtain an external oblique view of the pelvis. As shown in FIG. 4A, the fluoroscopy system 100 (C-arm 120) is tilted around the cranio-caudal axis such that the plane of the acetabular cup rim is perpendicular to the plane of the image amplifier (which constitutes part of the C-arm 120). As shown in FIG. 4B, in this position, the acetabular rim looks linear and no longer has an elliptical appearance.

In other words, the C-arm 120 is moved (rotated about the patient) until the equatorial plane of the cup is perpendicular to the plane of the fluoroscopy receptor (image amplifier 101). In this position, the ellipse formed by the acetabular rim visually transitions into a line (FIG. 4B). The C-arm tilt (CaT) angle is then determined at that position by direct reading on the C-arm 120. In other words, the fluoroscopy system 100 itself calculates the angle of the C-arm 120 and the numerical value can be displayed on the console 130 or other display 190, or otherwise used to calculate the anteversion angle.

It will be appreciated that the process of determining the C-arm title angle can involve multiple steps in that movement of the C-arm 120 can be adjusted incrementally (e.g., rotated) until the desired position is obtained described herein. For example, the C-arm 120 can be initially moved to a predetermined, preselected position (i.e., a predetermined, preselected CaT angle) and the orientation and appearance of the acetabular rim is observed on the display (monitor 190) of the system 100. The position of the C-arm 120 is adjusted until the plane of the acetabular cup rim is perpendicular to the plane of the image amplifier 101 (part of the C-arm).

In one or more embodiments, the C-arm 120 is automatically moved in response to instructions from one or more of devices 105/109/130. In the desired target position of the C-arm 120 and illustrated in FIG. 4B, the acetabular rim appears linear and no longer has an elliptical appearance. Once the user observes this appearance of the acetabular rim, the surgeon can stop the movement of the C-arm 120 and the angle of the C-arm (CaT) is then measured and recorded.

Alternatively, the C-arm 120 can actuate automatically in response to a computer implemented system that automatically determines the appearance of the acetabular rim. For example, image comparison techniques (e.g., via an image comparison module) can be implemented or the characteristics of the rim can be analysed by calculating acetabular rim orientation and angles (as provided elsewhere herein). For example, a processor 150 configured with control console 130, mobile computing device 105 and/or server computing device 109 can execute a program that configures the device to store an initial image (e.g., image in FIG. 3B) representing the initial acetabular cup's orientation in a storage (e.g., memory 160). As the C-arm 120 moves to a different plane relative to the acetabular cup, the appearance of the rim on the display is altered and a subsequent image captured by the fluoroscopy system 100 is evaluated. The processor 150 evaluates the images of the rim of the acetabular cup, for example, to determine whether the rim appears linear or elliptical in shape. Once the rim appears linear, then the processor can instruct that an image be captured of the acetabular cup, for eventual use in calculating the anteversion angle. If the appearance of the rim remains elliptical, then the processor can instruct the C-arm 120 to further adjust the C-arm 120, thereby further altering the CaT angle of the C-arm 120.

The image comparison module thus compares a current radiographic image (which is displayed on the monitor in real time) with one or more previously captured and/or stored radiographic images. The comparison process can be continuous, or can in incremental and periodic steps. As mentioned herein, the target stop position of the C-arm 120 is a position in which the equatorial plane of the acetabular cup rim is perpendicular to the plane of the image amplifier 101 of the C-arm 120. It will be appreciated that the image analysis module is configured such that if the C-arm 120 is "over" pivoted and the rim of the acetabular cup appears linear, then the C-arm 120 is moved in an opposite direction (back toward the hip being replaced) and the above-described image comparison is performed until it is confirmed at what CaT angle the rim first appears linear in nature.

The image analysis module can be configured for substantially automatic control of the C-arm 120 in a non-uniform way in that the C-arm 120 is moved in increments until the target position is reached. Thus, initially the C-arm 120 can be moved in larger incremental angles; however, once the shape of the rim closes in on the target orientation (linear), the C-arm 120 is moved in much smaller increments (i.e., the C-arm 120 hones in on the target position).

Figure 3E:
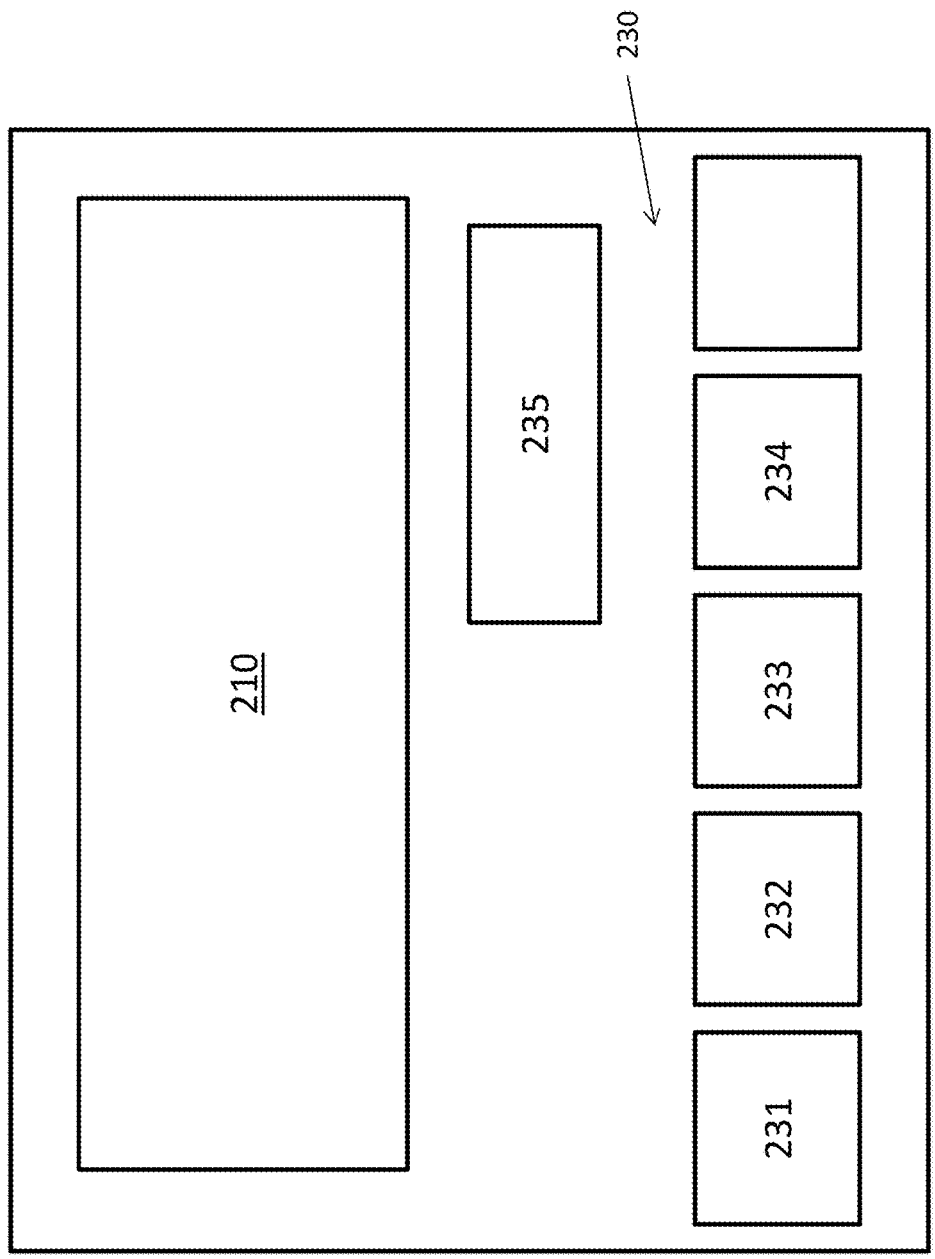
FIG. 3E is a representation of an exemplary graphical user interface in connection with an embodiment.

In one or more embodiments, the C-arm 120 is motorized and controllable by the user at the workstation or other device configured or associated with imaging system 100 (e.g., devices 105, 109 and 130). The movements of the C-arm 120 can be controlled, in certain embodiments, by the user through a virtual and graphical user interface (e.g., displayed on a monitor 190 or directly on mobile computing device 105 (e.g., a tablet). For example and as shown in FIG. 3E, an exemplary graphical user interface 230, which can be executed and displayed on the mobile computing device 200, includes a display 210 which can stream a live feed of radiographic images captured by the fluoroscopy system 100 (via C-arm 120). The user interface 230 can include various graphical screen controls, including but not limited to knobs, dials, buttons, checkboxes, dropdown lists, list boxes, toggles, text fields, and other navigational components including but not limited to slider, tags, icons, etc. In addition, the user interface 230 can include a program "start" button 231, a program "stop" button 232, "image capture and save" button 233 for results in capture of the current radiographic image, text field 234, etc. In addition, input controls can be provided to allow for manual control of the C-arm 120. In addition, the user interface 230 can include an output 235 which in this case can be the current tilt angle of the C-arm 120. Thus, the tilt angle of the C-arm 120 is displayed in real time as the C-arm 120 moves and assumes different positions. In addition, other input can be displayed. For example, the previously measured (calculated) inclination angle can be displayed to the user.

This measured CaT angle can then be inputted and saved in memory of the computing device or other hardware.

Determination of the Anteversion Angle

In accordance with the present invention, the intraoperative cup (acetabular component) anteversion is calculated based on the measured acetabular component abduction angle and the measures C-arm tilt angle (CaT). In one or more embodiments, the intraoperative cup anteversion is automatically calculated by the control console 130 as the CV and CI angles are measured. More particularly, the following equation expresses the CV (angle) as a function of the CI (angle) and the CaT angle:

$$CV = \tan^{-1}[\tan(CaT)\sin(CI)]$$

The x-axis of the three-dimensional frame is perpendicular to the sagittal plane (FIG. 3A, arrow 51), the y-axis parallel to the cranio-caudal axis of the body of the patient (FIG. 3A, arrow 52) and the z-axis perpendicular to the coronal plane (FIG. 3A, arrow 53).

The equatorial plane of the cup, $\pi_{rim}$, passing through the origin, is defined by the inclination angle CI and anteversion angle CV (FIG. 1). The unit vector normal to this plane $\vec{n}_{rim}$ is expressed as follows in the xyz coordinate system:

$$\vec{n}_{rim} = \begin{bmatrix} \cos(CV)\sin(CI) \\ \cos(CV)\cos(CI) \\ \sin(CV) \end{bmatrix}$$

The acetabular cup rim becomes a line and no longer appears elliptical when the plane of the image amplifier $\pi_{ia}$ is perpendicular to $\pi_{rim}$. This condition is obtained when $\pi_{ia}$ is defined by the vectors $\vec{n}_{rim}$ and $\vec{y} = [0\ 1\ 0]$ (as the C-arm is tilted around the y-axis). The vector normal to $\pi_{ia}$, $\vec{n}_{ia}$ is equal to the cross product of $\vec{n}_{rim}$ and $\vec{y}$. Therefore, $$\vec{n}_{ia} = \begin{bmatrix} -\sin(CV) \\ 0 \\ \cos(CV)\sin(CI) \end{bmatrix}$$

The C-arm tilt angle CaT that needs to be applied to the C-arm to make the plane of the image amplifier perpendicular to the plane of the cup rim is the angle between the vector $\vec{n}_{ia}$ and the z-axis. Consequently, $$CaT = \angle(\vec{n}_{ia}, \vec{z}) = \cos^{-1}\frac{\vec{n}_{ia} \cdot \vec{z}}{\|\vec{n}_{ia}\|\|\vec{z}\|}$$

This formula leads to the relation between the inclination angle (expressed in degrees) CI $\in$[0; 90], the anteversion angle CV $\in$[0; 90], and the c-arm tilt angle CaT:

$$CaT = \cos^{-1}\left(\frac{\cos(CV)\sin(CI)}{\sqrt{\sin^2(CV) + (\cos(CV)\sin(CI))^2}}\right) \quad (1)$$

Using trigonometric identities, (1) can be rewritten as follows:

$$CaT = \tan^{-1}\left(\frac{\tan(CV)}{\sin(CI)}\right)$$

The equation (1) can also be rewritten to express CV as the dependent variable:

$$CV = \tan^{-1}[\tan(CaT)\sin(CI)]$$

Accordingly, the anteversion angle can be determined using the previously measured CI and CaT angles (inputs into the computer implemented system).

Figure 5:
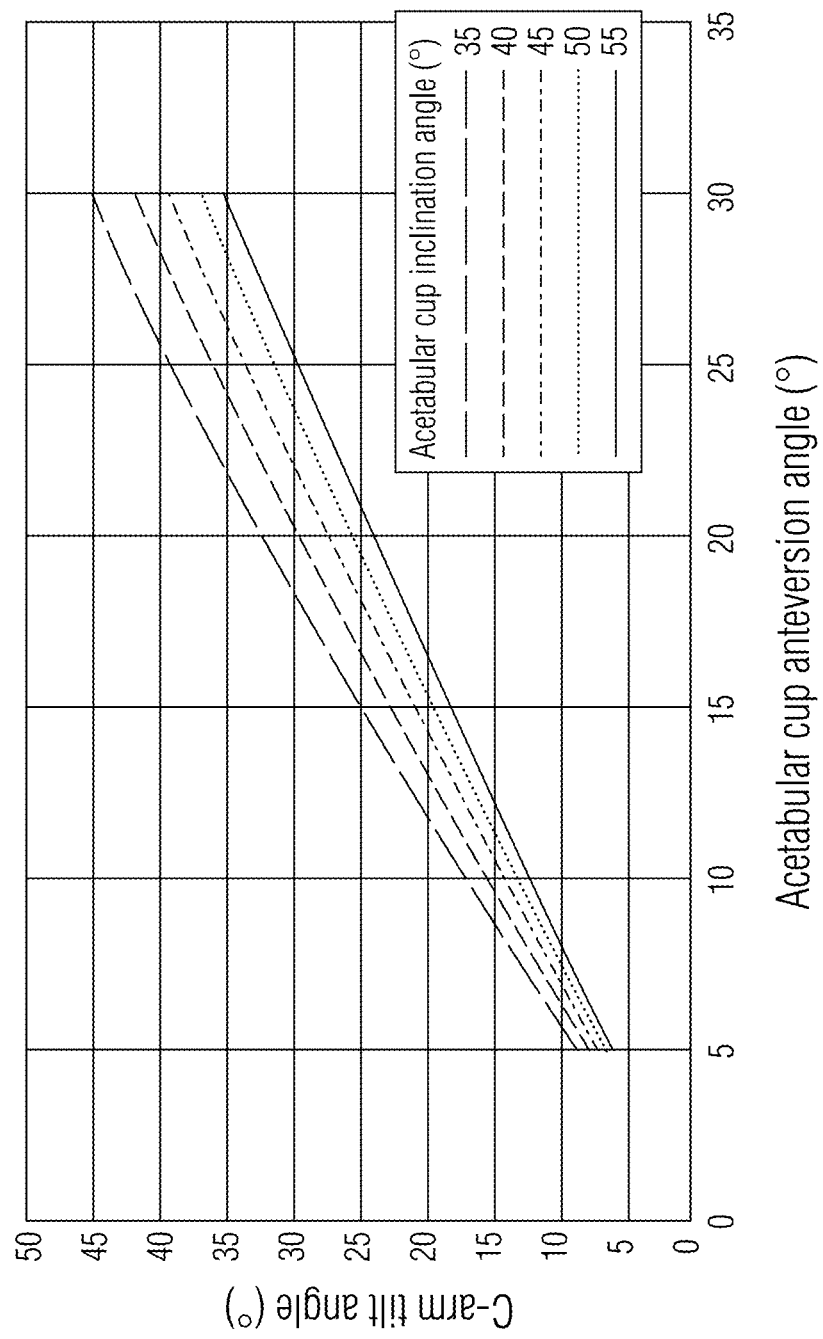
FIG. 5 is a graph illustrating that the C-arm tilt angle is a function of the acetabular cup abduction and anteversion angles.

To simplify the CV angle measurement, the CI and CaT angles can be reported on a chart such as the one illustrated in FIG. 5, which allows easy identification of the corresponding CV angle without using a calculator or computer processor. In other words, FIG. 5 shows a plot (graph) in which the x-axis identifies the acetabular cup anteversion angle and the y-axis identifies the C-arm tilt angle. Different abduction angle curves are plotted on the graph. For example, in FIG. 5, there are five exemplary acetabular cup inclination curves, namely 35°, 40°, 45°, 50°, and 55°.

Thus, for a given measures acetabular cup inclination curve there is a corresponding curve and the measured C-arm tilt angle can easily be located along the y axis. From these two data points, the anteversion angle can be read. For example, if the measured inclination angle is 40° and the measured C-arm title angle is 30°, then the surgeon (user) can easily report the value of the C-arm title angle (i.e., 30°) on the corresponding abduction angle curve (i.e., 40°) and read the anteversion angle.

Thus, FIG. 5 represents a numerical application of the above equation (1) in graph form to determine the anteversion angle when the acetabular CI and CaT angles are known. It will be appreciated that the graph is generated by plotting data that is generated by using the inputs and output of equation (1) and more specifically, it is generated by using the measured angles and the output of the equation (1).

FIG. 5 can thus represent output of the computing device 130, 109 which is displayed on the display (monitor 190).

The equation (1) and the subsequent exemplary curves presented in FIG. 5 demonstrate that the C-arm tilt angle necessary for the acetabular rim ellipse to appear linear tends towards the anteversion angle when the inclination angle tends towards 90°. Reciprocally, the lower the abduction angle, the greater is the difference between the C-arm tilt angle and the anteversion angle.

Thus, in accordance with at least one embodiment, a method for measuring the cup anteversion includes the steps of: (1) positioning the C-arm 120 perpendicular to the patient; (2) take an AP view of the pelvis in order to determine the cup abduction angle; (3) tilt the C-arm until the acetabular cup rim ellipse appears flat; and (4) report the value of the C-arm tilt angle on the corresponding abduction angle curve (FIG. 4) and read the anteversion angle. If the anteversion angle is not within a predefined acceptable range, such as a range disclosed herein, the surgeon will then reposition the acetabular cup and repeat steps (1) to (4). It will be appreciated that the repositioning of the acetabular cup will likely alter the inclination angle of the acetabular cup and thus, the CV angle will likewise be altered.

In another aspect of the present invention, surgeon guidance is provided by the computing device and in particular, if the calculated anteversion angle of the acetabular cup 10 is not acceptable to the surgeon, the surgeon can input a target anteversion angle and the processor can calculate the steps required to be taken by the surgeon to obtain such target anteversion angle. Since the C-arm 120 is at a known C-arm tilt angle and the target anteversion angle is known and is inputted, then the inclination angle can be determined to achieve such desired anteversion angle at a given C-arm tilt angle position. On the display of the mobile computing device or console or the workstation, etc., indicia can be displayed to guide the surgeon in the manual repositioning of the acetabular cup 10. For example, a coloured arrow can be depicted so show the direction of which the acetabular cup 10 should be moved and also the relative degree of movement can be displayed. For example, on the display, the indicia can be in the form of instructions to move 3° in a certain direction. In this way, the software receives the inputs and then outputs corrective instructions where needed to guide the surgeon in a manual repositioning of the cup.

Once the acetabular cup 10 is repositioned, then the steps disclosed herein can be performed again to determine the inclination angle and the anteversion angle of the cup 10 in its new position.

It will be appreciated that the target inclination and anteversion angles will vary from patient to patient; however, generally, a preferred inclination angle is between about 30° and about 50° and more preferably between 35° and about 45° (e.g., between about 38° and about 42° and in one embodiment is about 40°) and the anteversion angle can be between about 5° and about 30° and more preferably between about 15° to about 25° and more preferably between about 15° to about 20°.

EXAMPLE

A size 52 acetabular cup (Versafitcup®, Medacta, Castel San Pietro, Switzerland) was randomly positioned in the right acetabulum of a radiopaque pelvis (Ref. PR1102.9 Pelvis L4-L5 Femur prox. L/R, Synbone AG, Malans, Switzerland) and secured using a special rubber tape. The CV evaluation technique of the present invention was compared to CT-scan measurements. The pelvic model was positioned supine on a radiolucent CT-scan table. Care was taken to securely fix the pelvis on the table, so that the supine pelvic tilt angle did not vary between the fluoroscopic and CT measurements. A C-arm (Ziehm Vision®, Ziehm imaging GMBH, Germany) was placed perpendicular to the table. An AP pelvis radiograph (FIG. 3B) and the C-arm tilt angle were obtained (FIG. 4B). In addition, the number of images and time between the first and last image required to determine the CaT angle measurement were documented. Once the C-arm assessment was completed, CT-scan imaging of the pelvic model was obtained (64-MDCT scanner Discovery 750 HD, GE Healthcare, U.K.). Finally, the acetabular component position was randomly changed and the experiment was repeated 25 times.

Using a multipurpose DICOM viewer (OsiriX, Pixmeo Labs, Geneva, Switzerland), the CI was measured on the C-arm AP radiograph (angle between a reference line passing through the teardrops and the longitudinal axis of the cup), and the CV was calculated based on the equation (1) set forth herein. With the same DICOM viewer, using appropriate window settings (window level 300 and window width 2000), the aCV angle was evaluated on CT-scan images (FIG. 2) by an experienced radiologist (SB) who was blinded to the results of the experimental CV angles measurements. aCV corresponds to the angle between a reference line passing through the ischial spines and a line perpendicular to the equatorial plane of the cup. The control CV angle was computed and compared to the experimental CV angle (calculated with equation (1)).

Descriptive statistics were obtained for angles as well as for time lapse and number of images. The association of the control and experimental CV angles was evaluated graphically in a scatter plot and further assessed in a Bland-Altman plot with limits of agreement located at ±1.96 standard deviations (SD). Finally, the agreement between both methods was assessed using a linear regression method. Tests results with p values≤0.05 (two-tailed) were considered significant. Statistical analysis was conducted using Stata® 13 (StataCorp, College Station, Tex., USA).

The cup position was changed 25 times. The mean CI angle (SD, range) was 37.7° (6.2, 23-49). The mean CV angle (SD, range) measured with the experimental technique was 16.3° (7.1, 3.5-31.8). The mean CV angle (SD, range) determined using CT imaging was 16.1° (6.9, 4.3-34.0). The median number of images required to find the CaT angle was 6 (range 3-12), and the median time between the first and the last image taken was 13 seconds (range 7-33).

Figure 6:
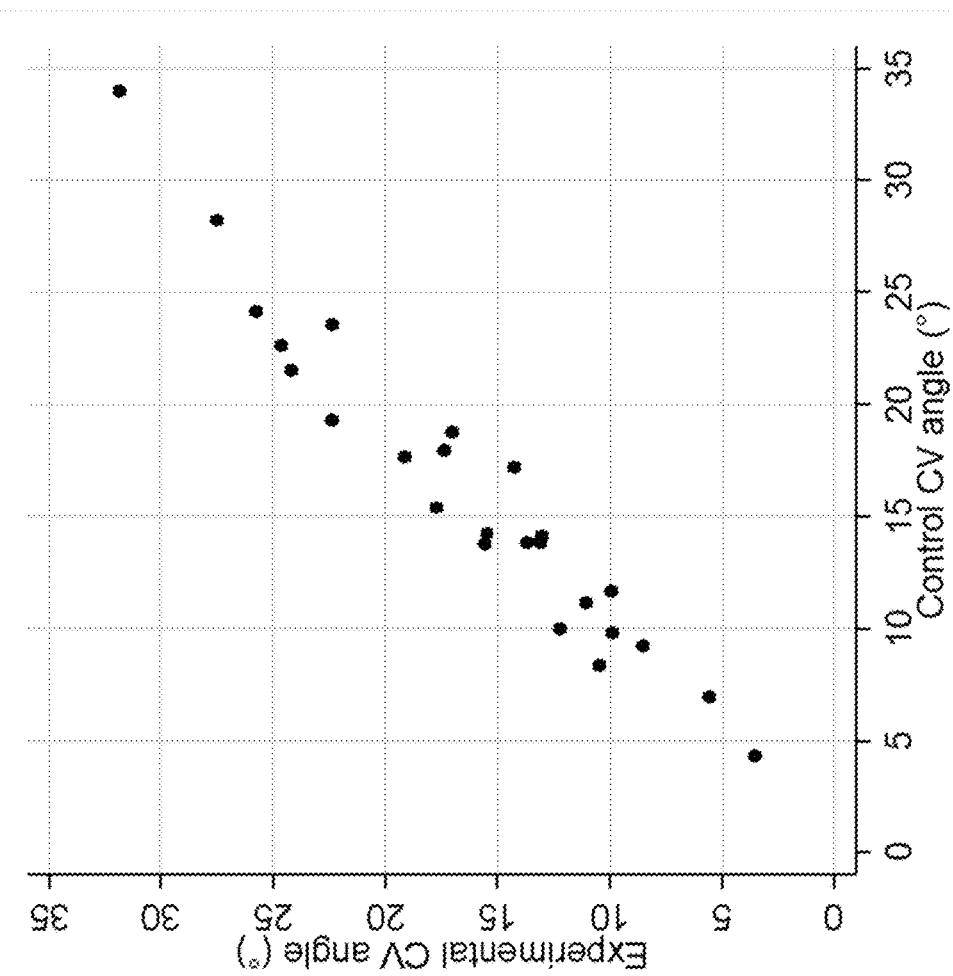
FIG. 6 is a scatter plot of control vs. experimental version angle.
Figure 7:
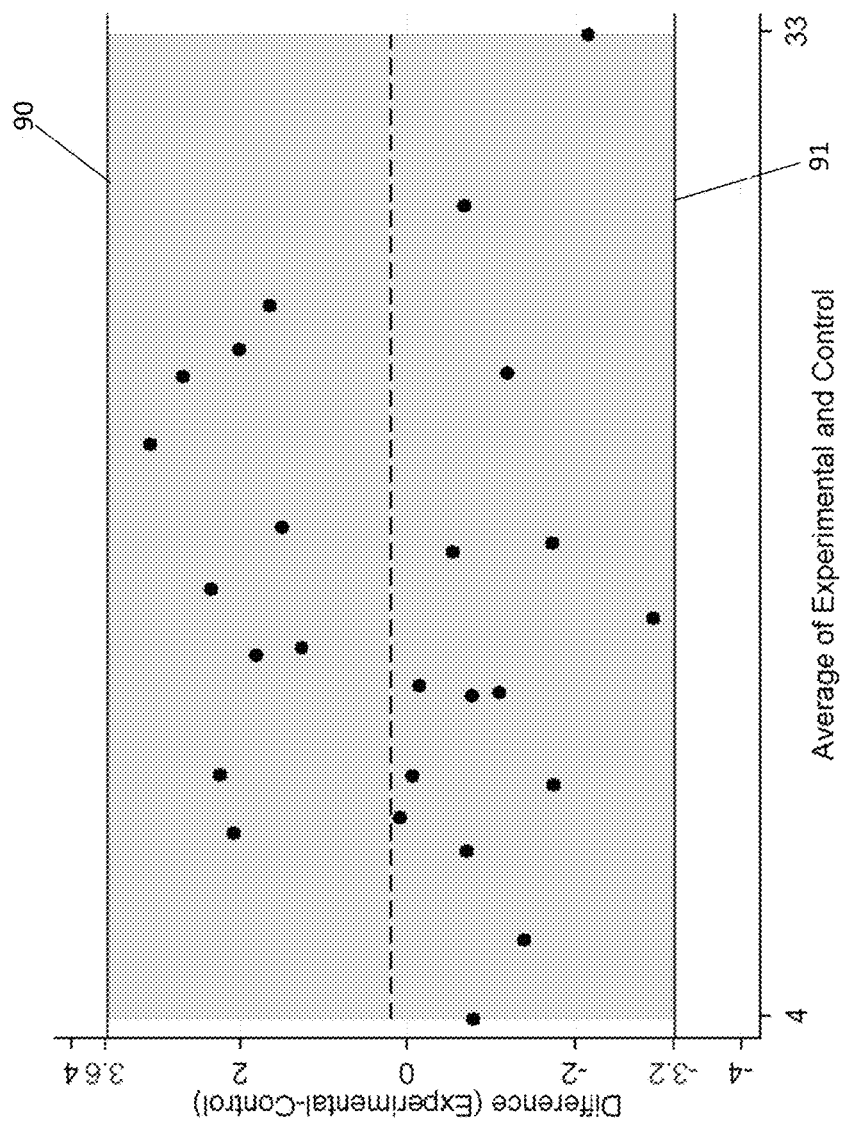
FIG. 7 is a Bland-Altman plot of control and experimental CV angles (°), with mean and limits of agreement (±1.96 SD, lines 90, 91).

The CV angle measured with the current technique was on average 0.2° (range −3.0-3.1) greater than the CV angle measured using the control method. The scatter plot of experimental vs. control CV angles shows excellent correlation between the two methods (FIG. 6). The agreement between the measures was assessed with a Bland-Altman plot (FIG. 7). None of the 25 measurements lay outside the limits of agreement. The linear regression coefficients evaluating the agreement between the experimental and control methods were 0.99 (95% CI 0.88-1.10, p<0.001) and 0.33 (95% CI −1.53-2.20, p=0.713) for the slope and intercept, respectively. In FIG. 7, the mean and limits of agreement (±1.96 SD) are shown by lines 90, 91.

The agreement between both methods is therefore excellent.

Advantages of the Present Invention

The current study confirms that the described three-step C-arm acetabular cup measuring technique can reproducibly and reliably assess acetabular component anteversion in the supine position, as compared to CT-imaging. Its impact on surgery time and radiation exposure is minimal.

Acetabular cup positioning has been given increasing attention since total hip arthroplasty was introduced. In 1978, Lewinnek et al., reported an increased rate of dislocations in patients who had an acetabular component positioned outside the "safe zone" corresponding to 30-50° inclination and 5-25° anteversion, and recommended to position the cup within these ranges. Since then, the existence of a universal safe zone has been questioned and recent studies reported that THA dislocations are more likely multifactorial and can occur with cups positioned within the so called safe zone. Nevertheless, guidelines issued by researchers and implant manufacturers recommend an acetabular cup position corresponding approximately to Lewinnek's safe zone. However, there are numerous reports that a large percentage of cups are positioned outside the reported safe zone and even experienced surgeons report outliers in more than 10 percent of cases according to certain studies.

Imaging tools capable of assessing the postoperative cup position have been developed. Among those, CT-scan remains the gold standard when very accurate measurements or advanced biomechanical studies are necessary. In order to verify the postoperative implant position in a routine manner, conventional imaging is generally sufficient, as the CI and CV angles can be directly assessed on AP and crosstable radiographs, respectively. Techniques aiming at evaluating the CV angle on AP pelvic radiographs have been developed over the years. A study by Nho et al. assessed six techniques based on conventional AP radiographs and compared them to CT-scan measurements. These techniques take advantage of the hemispherical nature of the cup. They demonstrated that the methods proposed by Lewinnek, Hassan and Liaw are reliable and correlate well with CT-scan measurements. The main constraints of these techniques are that they require (1) a standardized AP view of sufficient quality, and (2) accurate "on-film" measurements (either with a ruler and/or protractor, or with help of a dedicated software). Placing the patient in a lateral position as required for the posterior approach has increased the variability in CV and CI angle measurements between peri- and postoperative images up to 15°. The development of DAA THA with the patient in a supine position on a radiolucent operating table has greatly facilitated the use of intraoperative fluoroscopy. Rathod et al. achieved better cup positioning while performing DAA THA with c-arm assistance (using the method of Liaw et al. to assess CV) than through a posterior approach. Targeted CI and CV angles were respectively within the targeted range in 98% and 97% of the cases with DAA vs. only 86% and 77% for the posterior approach.

Applicant respectfully submits that the method (technique) of the present invention will demonstrate similar results while avoiding perioperative on-screen measurements. In summary, the present invention is directed to a highly accurate technique to intraoperatively determine acetabular component anteversion with the patient in the supine position.

Robotic Surgical System with Navigation

It will be understood that in one aspect of the present invention, a robotic surgical system can implement the equipment and methods described herein. More specifically, as shown in FIG. 3D, the robotic surgical system can include the robotic arm 75. As previously mentioned, the location of the patient and the surgical equipment (e.g., robotic arm 75 or navigated instrument (e.g., navigated cup inserter)) can be tracked using conventional navigational techniques, such as the placement of tracking elements on the equipment and patient. In this manner, the precise location of the patient and the robotic arm 75 is captured and tracked.

In one aspect of the present invention, positioning and movement of the acetabular cup 10 is controlled by the robotic arm 75. Thus, if the after performing the steps described herein, the calculated anteversion angle is not acceptable, the user (surgeon) can instruct repositioning of the acetabular cup 10 by means of a user interface which generates input control commands for controlling the robotic arm 75 or alternatively, the software of the computing device can calculate the adjustment of the acetabular cup 10 that is desired and then send command signals to the robotic arm 75 to control movement thereof resulting in repositioning the acetabular cup 10.

It is to be understood that like numerals in the drawings represent like elements through the several figures, and that not all components and/or steps described and illustrated with reference to the figures are required for all embodiments or arrangements. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Various modifications and changes can be made to the subject matter described herein without following the example embodiments and applications illustrated and described, and without departing from the true spirit and scope of the present invention, as set forth in each and any of the following claims.

What is claimed is:

1. A fluoroscopy-based method for measuring intraoperative acetabular cup anteversion during total hip arthroplasty utilizing a direct anterior approach (DAA) comprising the steps of:

(A) processing, by a computing device configured by executing code stored in non-transitory processor readable media, an anterior posterior image of a pelvis that includes an initially positioned acetabular cup, to measure an abduction angle of the acetabular cup, wherein the anterior posterior image is taken by a fluoroscopy image capture device configured with a C-arm;

(B) processing, by the computing device, an external pelvic oblique image that includes the acetabular cup and that is taken by the fluoroscopy image capture device and positioned relative to a plane of the acetabular cup's rim to detect whether a plane of an image amplifier of the fluoroscopy image capture device is positioned perpendicular to the plane of the acetabular cup's rim;

(i) where the plane of the image amplifier of the fluoroscopy image capture device is detected, by the computing device, to be not positioned perpendicular to the plane of the acetabular cup's rim:

(a) transmitting, by the computing device, an instruction to move the C-arm to a different position and in a direction away from a hip of a patient that is being replaced with an implant including the acetabular cup;

(b) processing, by the computing device, a subsequently captured external pelvic oblique image that includes the acetabular cup and that is taken by the fluoroscopy image capture device to detect whether the plane of the image amplifier is positioned perpendicular to the plane of the acetabular cup's rim; and (c) repeating, by the computing device, steps (A) and (B); and (ii) where the plane of the image amplifier of the fluoroscopy image capture device is detected, by the computing device, to be positioned perpendicular to the plane of the acetabular cup's rim:

(a) recording, by the computing device, a C-arm tilt angle when the C-arm is in a position in which the plane of the image amplifier is perpendicular to the plane of the acetabular cup's rim;

(b) calculating, by the computing device, an anteversion angle based on the measured abduction angle and the recorded C-arm tilt angle;

(c) determining, by the computing device, whether the calculated anteversion angle is within a predetermined acceptable range; and (d) where the calculated anteversion angle is outside of the predetermined acceptable angle, repeating, by the computing device, steps (a)-(d) until the calculated anteversion angle is within the predetermined acceptable range.

2. The method of claim 1, wherein the C-arm is positioned in an initial position parallel to a longitudinal axis of a surface supporting the patient during the capturing of the anterior posterior image.

3. The method of claim 1, wherein the anterior posterior image of the pelvis is processed, by the computing device, to measure the abduction angle as a function of a virtual protractor.

4. The method of claim 1, wherein the plane of the image amplifier is detected, by the computing device, to be not positioned perpendicular to the plane of the acetabular cup's rim as a function of detecting an elliptical appearance of the acetabular cup's rim.

5. The method of claim 1, wherein the plane of the image amplifier is detected, by the computing device, to be positioned perpendicular to the plane of the acetabular cup's rim as a function of detecting a linear appearance of the acetabular cup's rim.

6. A fluoroscopy-based system for measuring intraoperative acetabular cup anteversion during total hip arthroplasty utilizing a direct anterior approach (DAA), the system comprising:

a computing device configured with a processor and non-transitory processor readable memory that includes programming code that, when executed, configures the processor to:

(A) process an anterior posterior image of a pelvis that includes an initially positioned acetabular cup, to measure an abduction angle of the acetabular cup, wherein the anterior posterior image is taken by a fluoroscopy image capture device configured with a C-arm;

(B) process an external pelvic oblique image that includes the acetabular cup and that is taken by the fluoroscopy image capture device and positioned relative to a plane of the acetabular cup's rim to detect whether a plane of an image amplifier is positioned perpendicular to the plane of the acetabular cup's rim;

(i) where the plane of the image amplifier of the fluoroscopy image capture device is detected to be not positioned perpendicular to the plane of the acetabular cup's rim:

(a) transmit an instruction to move the C-arm to a different position and in a direction away from a hip of a patient that is being replaced with an implant including the acetabular cup;

(b) process a subsequently captured external pelvic oblique image that includes the acetabular cup and that is taken by the fluoroscopy image capture device to detect whether the plane of the image amplifier is positioned perpendicular to the plane of the acetabular cup's rim; and (c) repeat steps (A) and (B); and (d) where the plane of the image amplifier of the fluoroscopy image capture device is detected to be positioned perpendicular to the plane of the acetabular cup's rim:

(a) record a C-arm tilt angle when the C-arm is in a position in which the plane of the image amplifier is perpendicular to the plane of the acetabular cup's rim;

(b) calculate an anteversion angle based on the measured abduction angle and the recorded C-arm tilt angle;

(c) determine whether the calculated anteversion angle is within a predetermined acceptable range; and (d) where the calculated anteversion angle is outside of the predetermined acceptable angle, repeat steps (a)-(d) until the calculated anteversion angle is within the predetermined acceptable range.

7. The system of claim 6, wherein the C-arm is positioned in an initial position parallel to a longitudinal axis of a surface supporting the patient during the capturing of the anterior posterior image.

8. The system of claim 6, wherein the anterior posterior image of the pelvis is processed to measure the abduction angle as a function of a virtual protractor.

9. The system of claim 6, wherein the plane of the image amplifier is detected, by the computing device, to be not positioned perpendicular to the plane of the acetabular cup's rim as a function of detecting an elliptical appearance of the acetabular cup's rim.

10. The method of claim 1, wherein the anteversion angle is calculated using the following equation:

$$CV=\tan^{-1}[\tan(CaT)\sin(CI)]$$

wherein CV is the anteversion angle, CaT is the C-arm tilt angle, and the CI is the abduction angle.

11. The method of claim 1, wherein the predetermined acceptable range for the anteversion angle is between about 5° and about 25°.

12. The method of claim 1, wherein the predetermined acceptable range for the anteversion angle is between about 15° and about 20°.

13. The method of claim 1, further comprising plotting, by the computing device, an abduction curve along a graph that has an x-axis along which the C-arm tilt angle is listed and a y-axis along which the anteversion angle is listed.

14. The method of claim 1, further comprising displaying, by the computing device, an anterior posterior (AP) radiographic image of a pelvis and an external pelvic oblique radiographic image on a display associated with the C-arm fluoroscopy system.

15. The system of claim 6, wherein the anteversion angle is calculated using the following equation:

$$CV=\tan^{-1}[\tan(CaT)\sin(CI)]$$

wherein CV is the anteversion angle, CaT is the C-arm tilt angle, and the CI is the abduction angle.

16. The system of claim 6, wherein the predetermined acceptable range for the anteversion angle is between about 5° and about 25°.

17. The system of claim 6, wherein the predetermined acceptable range for the anteversion angle is between about 15° and about 20°.

18. The system of claim 6, wherein the non-transitory processor readable memory further includes programming code that, when executed, configures the processor to plot an abduction curve along a graph that has an x-axis along which the C-arm tilt angle is listed and a y-axis along which the anteversion angle is listed.

19. The system of claim 6, wherein the non-transitory processor readable memory further includes programming code that, when executed, configures the processor to display an anterior posterior (AP) radiographic image of a pelvis and an external pelvic oblique radiographic image on a display associated with the C-arm fluoroscopy system.

20. A fluoroscopy-based system for measuring intraoperative acetabular cup anteversion during total hip arthroplasty utilizing a direct anterior approach (DAA), the system comprising:
 a computing device configured with a processor and non-transitory processor readable memory that includes programming code that, when executed, configures the processor to:
(A) process an anterior posterior image of a pelvis that includes an initially positioned acetabular cup, to measure an abduction angle of the acetabular cup, wherein the anterior posterior image is taken by a fluoroscopy image capture device configured with a C-arm;
(B) process an external pelvic oblique image that includes the acetabular cup and that is taken by the fluoroscopy image capture device and positioned relative to a plane of the acetabular cup's rim to detect whether the shape of acetabular cup's rim appears linear;
 (i) where the shape of acetabular cup's rim does not appear linear:
  (a) transmit an instruction to move the C-arm to a different position and in a direction away from a hip of a patient that is being replaced with an implant including the acetabular cup;
  (b) process a subsequently captured external pelvic oblique image that includes the acetabular cup and that is taken by the fluoroscopy image capture device to detect whether the shape of acetabular cup's rim appears linear; and
  (c) repeat steps (A) and (B); and
 (ii) where the shape of acetabular cup's rim appears linear:
  (a) record a C-arm tilt angle when the C-arm is in a position in which the shape of acetabular cup's rim appears linear;
  (b) calculate an anteversion angle based on the measured abduction angle and the recorded C-arm tilt angle;
  (c) determine whether the calculated anteversion angle is within a predetermined acceptable range; and
  (d) where the calculated anteversion angle is outside of the predetermined acceptable angle, repeat steps (a)-(d) until the calculated anteversion angle is within the predetermined acceptable range.

* * * * *

UNITED STATES PATENT AND TRADEMARK OFFICE
CERTIFICATE OF CORRECTION

PATENT NO. : 10,238,454 B2
APPLICATION NO. : 15/501671
DATED : March 26, 2019
INVENTOR(S) : Friedrich Boettner and Matthieu Zingg Page 1 of 1

It is certified that error appears in the above-identified patent and that said Letters Patent is hereby corrected as shown below:

In the Claims

Column 17, Line 50, Claim 1, the text -by the computing device, steps (a)-(d) until the- should read --by the computing device, steps (A) and (B) until the--
Column 18, Line 53, Claim 6, the text -the predetermined acceptable angle, repeat steps (a)-(d)- should read --the predetermined acceptable angle, repeat steps (A) and (B)--
Column 20, Line 43, Claim 20, the text -steps (a)-(d) until the calculated anteversion angle- should read --steps (A) and (B) until the calculated anteversion angle--

Signed and Sealed this
Seventeenth Day of March, 2020

Andrei Iancu
*Director of the United States Patent and Trademark Office*